United States Patent
Margolis et al.

(10) Patent No.: US 6,514,979 B1
(45) Date of Patent: Feb. 4, 2003

(54) SYNERGISTIC COMBINATIONS OF GUANOSINE ANALOG REVERSE TRANSCRIPTASE INHIBITORS AND INOSINE MONOPHOSPHATE DEHYDROGENESE INHIBITORS AND USES THEREFOR

(75) Inventors: David Margolis, Baltimore, MD (US); Alonso Heredia, Washington, DC (US); David Oldach, Towson, MD (US); Robert Redfield, Baltimore, MD (US)

(73) Assignee: University of Maryland Biotechnology Institute, College Park, MD (US)

( * ) Notice: Subject to any disclaimer, the term of this patent is extended or adjusted under 35 U.S.C. 154(b) by 0 days.

(21) Appl. No.: 09/261,712

(22) Filed: Mar. 3, 1999

(51) Int. Cl.⁷ ...................... A61K 31/52; A61K 31/505; A61K 31/34
(52) U.S. Cl. .................. 514/261; 514/266; 514/470
(58) Field of Search ............................... 514/261, 266, 514/470

(56) References Cited

U.S. PATENT DOCUMENTS

| | | | |
|---|---|---|---|
| 4,686,234 A | 8/1987 | Nelson et al. | 514/469 |
| 4,725,622 A | 2/1988 | Nelson et al. | 514/469 |
| 4,727,069 A | 2/1988 | Nelson et al. | 514/211 |
| 4,748,173 A | 5/1988 | Nelson et al. | 514/211 |
| 4,753,935 A | 6/1988 | Nelson et al. | 514/233.5 |
| 4,786,637 A | 11/1988 | Allison et al. | 514/233.5 |
| 4,808,592 A | 2/1989 | Nelson et al. | 514/233.5 |
| 4,861,776 A * | 8/1989 | Nelson et al. | 514/233.5 |
| 5,034,394 A * | 7/1991 | Daluge | 514/261 |
| 5,049,671 A | 9/1991 | Daluge | 514/261 |
| 5,070,078 A | 12/1991 | Selway et al. | 514/261 |
| 5,087,697 A | 2/1992 | Daluge | 544/323 |
| 5,089,500 A | 2/1992 | Daluge | 514/261 |
| 5,206,435 A | 4/1993 | Daluge | 544/247 |
| 5,380,879 A * | 1/1995 | Sjogern | 549/310 |
| 5,399,580 A | 3/1995 | Daluge | 514/261 |
| 5,441,953 A | 8/1995 | Sjogren | 514/223.5 |
| 5,444,072 A | 8/1995 | Patterson et al. | 514/320 |
| 5,493,030 A | 2/1996 | Morgans, Jr. et al. | 548/230 |
| 5,534,535 A | 7/1996 | Townsend et al. | 514/261 |
| 5,536,747 A | 7/1996 | Patterson et al. | 514/470 |
| 5,538,969 A | 7/1996 | Morgans, Jr. et al. | 514/233.5 |
| 5,554,612 A | 9/1996 | Patterson et al. | 514/233.5 |
| 5,574,149 A | 11/1996 | Van Tuttle et al. | 514/261 |
| 5,631,370 A | 5/1997 | Vince et al. | 544/244 |
| 5,633,279 A | 5/1997 | Morgans, Jr. et al. | 514/468 |
| 5,637,574 A | 6/1997 | Burns et al. | 514/45 |
| 5,641,889 A | 6/1997 | Daluge et al. | 564/1 |
| 5,807,876 A | 9/1998 | Armistead et al. | 514/374 |
| 5,808,147 A | 9/1998 | Daluge et al. | 562/504 |
| 5,840,990 A | 11/1998 | Daluge et al. | 564/507 |

FOREIGN PATENT DOCUMENTS

WO   WO 94/12184   6/1994

OTHER PUBLICATIONS

Lori, et al. "Hydroxyurea as an Inhibitor of Human Immunodeficiency Virus–Type 1 Replication." Science. vol. 266. pp. 801–805. Nov. 4, 1994.

Ichimura et al. "Polymerase Substrate Depletion: A Novel Strategy for Inhibiting the Replication of the Human Immunodeficiency Virus." Virology. vol. 211. pp. 554–560. 1995.

Malley et al. "Synergistic Anti–Human Immunodeficiency Virus Type 1 Effect of Hydroxamate Compounds with 2',3'–Dideoxyinosine in Infected Vesting Human Lymphocytes." Proc. Natl. Acad. Sci. USA. vol. 91. pp. 110117–11021. Nov. 1994.

Gao et al. "Low Levels of Deoxynucleotides in Peripheral Blood Lymphocytes: A Strategy to Inhibit Human Immunodeficiency Virus Type 1 Replication." Proc. Natl. Acad. Sci. USA. vol. 90. pp. 8925–8928. Oct. 1993.

Malley et al. "Suppression of HIV Production in Resting Lymphocytes by Combining Didanosine and Hydroxamate Compounds." The Lancet. vol. 343. p. 1292. May 21, 1994.

Vila et al. "1–year Follow–up of the Use of Hydroxycarbamide and Didanosine in HIV Infection." The Lancet. vol. 348. pp. 203–204. Jul. 29, 1996.

Vila et al. "Absence of Viral Rebound After Treatment of HIV–Infected Patients with Didanosine and Hydroxycarbamide." The Lancet. vol. 350. p. 635–636. Aug. 30, 1997.

Lori et al. "Hydroxyurea as an Inhibitor of Human Immunodeficiency Virus–Type 1 Replication." Science. vol. 266. pp. 801–805. Nov. 4, 1994.

Draft Product Information on Ziagen™. Dec. 17, 1998.

Lesiak et al. "Synthesis of a Methoylenebis (phosphonate) Analogue of Mycophenolic Adenine Dinucleotide: A Glucuronidation–Resistant MAD Analogue of NAD." Journal of Medicinal Chemistry. vol. 41. No. 4. pp. 618–622. 1998.

Randall E. Morris. "Mechanisms of Action of New Immunosuppressive Drugs." Therapeutic Drug Monitoring. vol. 17. No. 6. pp. 564–569. 1995.

John T. Ransom. "Mechanism of Action Mycophenolate Mofetil." Therapeutic Drug Monitoring. vol. 17. No. 6. pp. 681–684. 1995.

James J. Lipsky. "Mycophenolate Mofetil." The Lancet. vol. 348. pp. 1357–1359. Nov. 16, 1996.

* cited by examiner

*Primary Examiner*—Russell Travers
(74) *Attorney, Agent, or Firm*—Marianne Fuierer; Steven J. Hultquist; Yongzhi Yang

(57) ABSTRACT

Synergistic combinations of guanosine nucleoside analog reverse transcriptase inhibitors such as abacavir with inosine monophosphate dehydrogenase inhibitors such as mycophenolates, pharmaceutical compositions comprising such combinations, and therapeutic methods comprising administering the synergistic combinations to subjects in need thereof, for treating a viral infection, such as an HIV-1 infection.

10 Claims, 6 Drawing Sheets

SYNERGISTIC COMBINATIONS OF GUANOSINE ANALOG REVERSE TRANSCRIPTASE INHIBITORS AND INOSINE MONOPHOSPHATE DEHYDROGENESE INHIBITORS AND USES THEREFOR

BACKGROUND OF THE INVENTION

1. Field of the Invention

The present invention relates generally to synergistic combinations of guanosine analog reverse transcriptase inhibitors (GA-RTI), such as abacavir, with potent inosine monophosphate dehydrogenase (IMPDH) inhibitors such as mycophenolic acid, its derivatives and related compounds, pharmaceutical compositions comprising such combinations and therapeutic methods comprising administering such combinations to patients in need thereof, for treating a viral infection, such as an HIV-1 infection.

2. Description of the Related Art

Acquired Immunodeficiency Syndrome (AIDS) is an immunosuppressive or immunodestructive disease that predisposes subjects to fatal opportunistic infections. Characteristically, AIDS is associated with a progressive depletion of T-cells. Human immunodeficiency virus (HIV) has been reproducibly isolated from patients with AIDS or with the symptoms that frequently precede AIDS. HIV is cytopathic and preferentially infects and destroys T-cells, and it is now generally recognized that HIV is the etiological agent of AIDS.

Anti-HIV therapies have generally taken the approach of inhibiting or blocking functions that are specific to HIV, e.g., functions that are necessary in the viral lifecycle but are not part of the host cell's metabolism, for example specific viral protease inhibition, viral RNA-to-DNA transcription.

HIV is a retrovirus and consequently employs the viral enzyme reverse transcriptase to transcribe its single-stranded RNA into double-stranded DNA competent for integration and the completion of the viral lifecycle. Interruption of this step prevents viral replication. Potent and selective inhibitors of reverse transcriptase have been identified and shown to have utility in anti-retroviral pharmaceutical compositions. These reverse transcriptase inhibitors (RTI's) generally fall into two broad classes, nucleoside analogs such as zidovudine and lamivudine, and the non-nucleoside reverse transcriptase inhibitors (NNRTI's) such as Efavirenz ((S)-6-chloro-4-(cyclopropylethynyl)-1,4-dihydro-4-(trifluoromethyl)-2H-3,1-benzoxazine-2-one, Sustiva®, Dupont Pharmaceuticals).

Nucleoside analog RTI's can be further classified based on the nucleoside that they mimic. For example, the well-known RTI's zidovudine, 3'-azido-3'-deoxythymidine (Retrovir®, formerly called azidothymidine (AZT), Glaxo Wellcome, Inc.), stavudine (2',3'-dihydro-3'-deoxythymidine, d4T, Zerit®), Bristol-Myers-Squibb Corp.), and lamivudine, (2R,cis)4-amino-1-(2-hydroxymethyl-1,3-oxathiolan-5-yl)-(1H)-pyrimidin-2-one (3TC, Epivir®, Glaxo-Wellcome) are pyrimidine nucleoside analogs that have been widely used alone and in combination in anti-retroviral pharmaceutical applications.

Purine nucleoside analogs have been identified that have useful reverse transcriptase inhibitory activity as well. Didanosine (2',3'-dideoxyinosine, DDI, Videx®, Bristol-Myers-Squibb Corp.) is an adenosine nucleoside analog that is used in RTI pharmaceutical compositions.

Recently the first guanosine nucleoside analogs that are potent reverse transcriptase inhibitors ("GA-RTI's") have been identified. Such GA-RTI's are described, e.g., in U.S. Pat. No. 5,089,500, "Therapeutic Nucleosides," issued Feb. 18, 1992; U.S. Pat. No. 5,034,394, entitled "Therapeutic Nucleosides," issued Jul. 23, 1991; and U.S. Pat. No. 5,087,697, same title, issued Feb. 11, 1992, the disclosures of all of which are hereby incorporated herein by reference in their respective entireties.

Abacavir (Ziagen™; (1 S,cis)4-[2-amino-6-(cyclopropylamino)-9H-purin-9-yl]-2-cyclopentene-1-methanol sulfate, Glaxo Wellcome, Inc.) is the first clinically available guanosine analog HIV-1 reverse transcriptase inhibitor. The most potent nucleoside analog yet developed, when studied in the setting of monotherapy abacavir resulted in a 1.55 log drop in plasma HIV-1 RNA (Ziagen package insert. Glaxo Wellcome, Inc., Research Triangle Park, N.C.). Other guanosine analogs are in development, e.g., DAPD (1-β-D-2,6-diaminopurine dioxolane; Triangle Pharmaceuticals, Inc., Research Triangle Park, N.C.).

HIV is wholly dependent on cellular deoxyribonucleoside triphosphate (dNTP) for the transcription of viral single-stranded RNA into double-stranded DNA competent for integration and the completion of the viral lifecycle. Viral dependence on host factors has been exploited as a novel approach to inhibit HIV-1 replication (e.g., Johns D G; Gao W Y, "Selective depletion of DNA precursors: an evolving strategy for potentiation of dideoxynucleoside activity against human immunodeficiency virus." Biochem Pharmacol. May 15, 1998 ;55(10):1551–6).

An unfortunate aspect of HIV infection is the ability of the virus to rapidly mutate and the frequency with which new strains arise with resistance to various drug therapies. Consequently, there is a need to develop new therapeutic approaches to anti-HIV treatment and. in particular, approaches that combine more than one viral target entity. Further, there is a need for approaches that combine one or more viral targets with inhibition of a host cell function or reduction of a host cell substance or factor which enables viral replication.

The present invention provides such a novel combination approach.

SUMMARY OF THE INVENTION

The present invention takes advantage of a surprising and powerful newly discovered synergistic effect between guanosine analog reverse transcriptase inhibitors ("GA-RTI") and potent inhibitors of the enzyme inosine monophosphate dehydrogenase (IMPDH), such as mycophenolic acid and analogs and their pharmaceutically acceptable salts, derivatives, and prodrugs (collectively, "mycophenolates"), to provide novel combinations having utility in the treatment of viral infections, especially in treating HIV infection.

The present invention provides therapeutic compositions comprising synergistically effective amounts of at least one GA-RTI compound and at least one IMPDH inhibitor, such as a mycophenolate compound.

In another aspect the present invention provides a novel composition for treating viral infection, such as a retroviral infection, comprising a pharmaceutically acceptable carrier and a synergistic combination of at least one GA-RTI compound and at least one IMPDH inhibitor, such as a mycophenolate compound.

In another aspect the present invention provides a novel method for treating or preventing a viral infection, such as an HIV infection, comprising administering to a subject in need thereof a therapeutically effective amount of a combination of at least one GA-RTI compound with at least one IMPDH inhibitor, such as a mycophenolate compound.

In preferred embodiments, the synergistic combinations of the invention comprise at least one compound selected from GA-RTI compounds of the general formula:

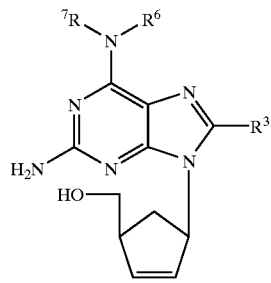

where
  $R^3$ represents hydrogen or $C_1-C_6$ alkyl;
  $R^6$ represents $C_{3-8}$ cycloalkyl;
  $R^7$ represents hydrogen or branched or straight chain $C_{1-6}$ alkyl;
or a pharmaceutically acceptable derivative thereof; in combination with at least one mycophenolate compound selected from mycophenolic acid, and pharmaceutically acceptable salts, derivatives, analogs and prodrugs of mycophenolic acid, which has the formula:

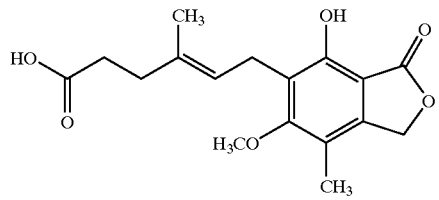

and where the GA-RTI compound(s) and the mycophenolate compound(s) are combined in amounts and proportions to yield a therapeutically effective composition for treatment of disease states mediated by retroviral infection.

The synergistic combinations of the present invention may further comprise pharmaceutical carriers.

DETAILED DESCRIPTION OF THE INVENTION, AND PREFERRED EMBODIMENTS THEREOF

Definitions

Figure 1A:
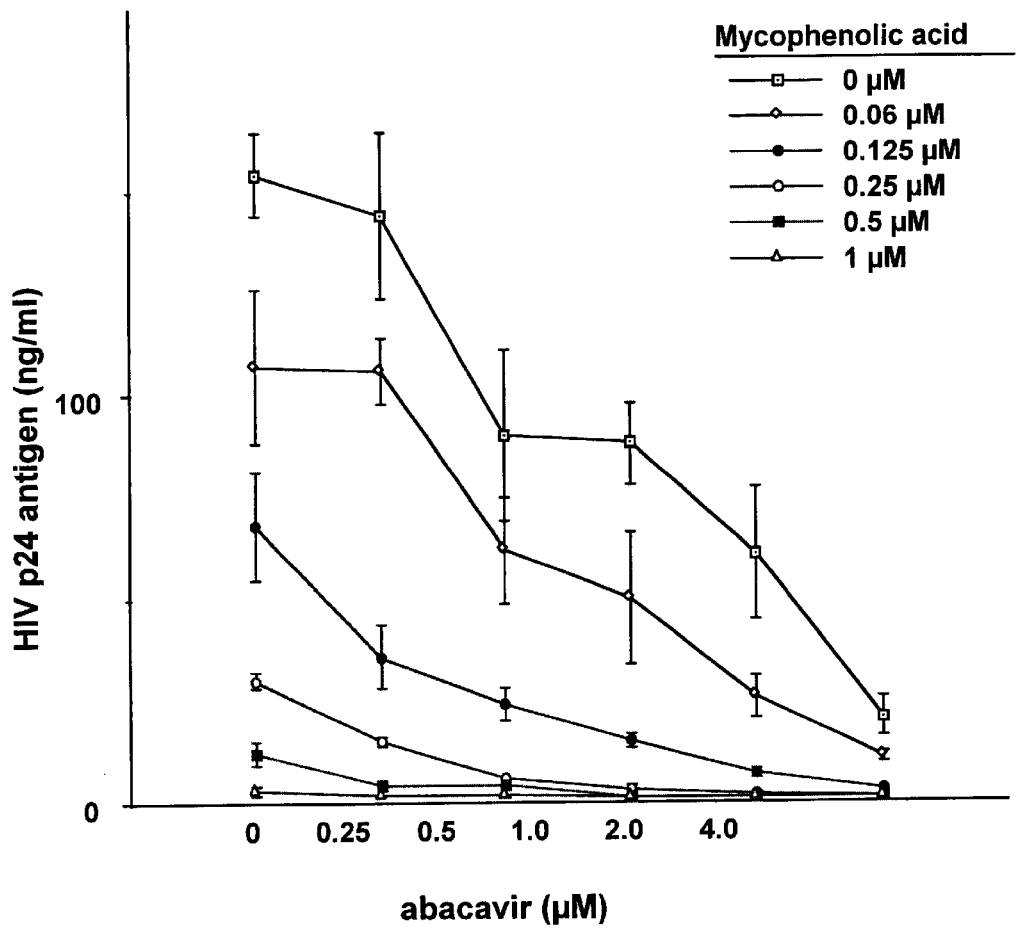
FIGS. 1A and 1B are plots of p24 production (a measure of HIV present) by HIV IIIb infected peripheral blood mononuclear cells (PBMCs) versus abacavir concentration ($\mu$M) at 0, 0.06, 0.125, 0.25, 0.5 and $\mu$M MA (FIG. 1A) and at 0, 0.125 and 0.500 $\mu$M MA (FIG. 1B)

The term "synergistic" as used herein means that the effect achieved with the compounds used together is greater than the sum of the effects that result from using the compounds separately. The GA-RTIs and IMPDH inhibitors described herein are sometimes referred to herein as the "synergistic ingredients" or the "synergistic compounds."

The degree of synergism of the combinations of the present invention was analyzed according to the definition of Loewe, using the interaction model of Greco et al. (Greco W. R, Bravo G., Parsons J. C. The search for synergy: a critical review from a response surface perspective. Pharmacol. Rev 1995;47:331–385.) to yield an interaction parameter alpha. This model is fully parametric, and point estimates of the model parameters are obtained in a traditional weighted, nonlinear least-squares approach. The model follows the equation below:

$$1 = \frac{D_1}{IC_{50.1} \cdot [E/(E_{con} - E)]^{1/m1}} + \frac{D_2}{IC_{50.2} \cdot [E/(E_{con} - E)]^{1/m2}} + \frac{\alpha \cdot D_1 \cdot D_2}{IC_{50.1} \cdot IC_{50.2} \cdot [E/(E_{con} - E)]^{(1/2m1+1/2m2)}}$$

where alpha ($\alpha$) is the synergism-antagonism interaction parameter, $IC_{50.1}$ and $IC_{50.2}$ are the drug concentrations resulting in 50% inhibition for drug 1 and drug 2, respectively; $D_1$ and $D_2$ are the concentration of drugs tested; $E_{con}$ is the control effect in the absence of either drug, E is the observed effect, and $m_1$ and $m_2$ are the slope parameters for each drug. If the estimate of $\alpha$ is zero, the drug combination is additive; if $\alpha$ is positive, the interaction is synergistic; if $\alpha$ is negative, the interaction is antagonistic. The estimate of $\alpha$ presents an associated 95% confidence interval. When the confidence interval does not overlap zero, this provides the statistical significance for the estimate of the interaction. That is, if the 95% confidence interval crosses zero, the interaction is additive. If it does not and $\alpha$ is positive, the interaction is significantly synergistic. If it does not and $\alpha$ is negative, the interaction is significantly antagonistic.

The term "synergistic combinations" refers herein to combinations characterized by an alpha parameter that is positive and for which the 95% confidence interval does not cross zero. In the practice of the present invention, the synergistic combinations preferably are characterized by an alpha interaction parameter that is greater than about 2, and more preferably by an alpha parameter that is greater than about 4.

The term "pharmaceutically acceptable derivative" is used herein to denote any pharmaceutically or pharmacologically acceptable salt, ester, amide or salt of such ester or amide of a synergistic compound according to the invention.

In the selection of the GA-RTI compounds for use in the synergistic combinations of the present invention, "pharmaceutically acceptable derivatives" may preferably be esters such as carboxylic acid esters in which the non-carbonyl moiety of the ester grouping is selected from straight or branched chain alkyl. e.g. n-propyl, t-butyl, n-butyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy or amino); sulfonate esters such as alkyl- or aralkylsulfonyl (e.g. methanesulfonyl); amino add esters (e.g. L-valyl or L-isoleucyl); and mono-, di- or triphosphate esters. The phosphate esters may be further esterified by, for example, a $C_{1-20}$ alcohol or reactive derivative thereof, or by a 2,3-di $C_{2-4}$ acyl glycerol.

With regard to the above-described guanosine analog esters, unless otherwise specified, any alkyl moiety present advantageously contains 1 to 18 carbon atoms, particularly 3 to 6 carbon atoms such as the pentanoate. Any aryl moiety present in such esters advantageously comprises a phenyl group.

With regard to the mycophenolate compounds for use in the synergistic combinations of the present invention, "pharmaceutically acceptable derivatives" may preferably be esters, and more preferably heterocycloalkyl esters, for example, morpholinoethyl esters.

A "prodrug" is intended to mean a compound that is converted under physiological conditions or by solvolysis or metabolically to a specified compound that is pharmaceutically active. In the context of the mycophenolate compounds for use in the synergistic combinations of the present invention, ester derivatives are prodrugs that are metabolized to mycophenolic acid.

A "pharmaceutically active metabolite" is intended to mean a pharmacologically active product produced through metabolism in the body of a specified compound.

Any reference herein to any of the above compounds also includes a reference to a pharmaceutically acceptable salt thereof.

A "pharmaceutically acceptable salt" is intended to mean a salt that retains the biological effectiveness of the free acids and bases of the specified compound and that is not biologically or otherwise undesirable. Examples of pharmaceutically acceptable salts include but are not limited to sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caprotes, heptanoates, propioltes, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, sulfamates, xylenesulfonates, phenylacetates, phenylpropionates, phenylbutyrates, citrates, lactates, gamma-hydroxybutyrates, glycollates, tartrates, methanesulfonates, propanesulfonates, naphthalene-1-sulfonates, naphthalene-2-sulfonates, and mandelates.

Some of the compounds described herein can exist in more than one tautomeric form, all of which are intended to be comprehended.

"Mycophenolates" refers herein to mycophenolic acid and its analogs, and their pharmaceutically acceptable salts, derivatives, prodrugs, and metabolites.

As used herein, "MA" refers specifically to the 2-morpholinoethyl ester of mycophenolic acid, mycophenolate mofetil (Cellcept®, Roche Laboratories).

"Analogs" is intended to mean compounds derived from a particular parent compound by straightforward substitutions that do not result in a substantial (i.e. more than 100×) loss in the biological activity of the parent compound, where such substitutions are modifications well-known to those skilled in the art, e.g., esterification, replacement of hydrogen by halogen, replacement of alkoxy by alkyl, replacement of alkyl by alkoxy, etc.

"Therapeutically effective combination" is intended to mean an amount of the inventive synergistic combination that, when administered to a patient in need of treatment, is sufficient to effect treatment for the disease condition alleviated by the GA-RTI/IMPDH inhibitor combination, e.g., a retroviral infection. Amounts of each of the synergistic components present in a therapeutically effective combination may not be therapeutically effective when administered singly. The amount of a given combination that will be therapeutically effective will vary depending on factors such as the particular combination employed, the particular virus and viral strain infecting the patient, the anti-retroviral treatment history of the patient, the age and health of the patient, and other factors.

"Treatment" refers to alleviation or prevention of symptoms of viral infection in a patient or the improvement of an ascertainable measurement associated with a particular viral infection, e.g., various cell, antigen and antibody assays.

Guanosine Analog Reverse Transcriptase Inhibitors

Nucleoside analog reverse transcriptase inhibitors typically have modifications to the ribose moiety, such as a substitution of the sugar ring with a carbocyclic ring ("carbocyclic compounds") or a diether ring, e.g. dioxolanyl group ("dioxolane compounds"), and may have minor modifications to the purine or pyrimidine ring as well. The guanosine analogs useful in the practice of the present invention can have any of these types of modifications.

Guanosine analog reverse transcriptase inhibitor (GA-RTI) compositions and their preparation and use are described, e.g., in U.S. Pat. No. 5,089,500, "Therapeutic Nucleosides," issued Feb. 18, 1992; U.S. Pat. No. 5,034,394, entitled "Therapeutic Nucleosides," issued Jul. 23, 1991; U.S. Pat. No. 5,087,697, same title, issued Feb. 11, 1992, the disclosures of all of which are hereby incorporated herein by reference in their respective entireties. These patents disclose 6-substituted purine carbocyclic nucleosides and their use in medical therapy, particularly in the treatment of HIV and HBV infections. Such nucleoside analogs include compounds of the formula (I):

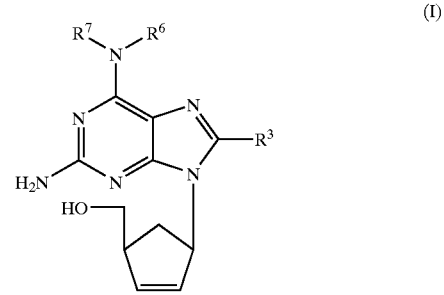

(I)

wherein $R^3$ represents hydrogen or $C_{1-6}$ alkyl;

$R^6$ represents $C_{3-8}$ cycloalkyl; and $R^7$ represents a hydrogen atom or branched or straight chain $C_{1-6}$ alkyl;

or a pharmaceutically acceptable derivative thereof.

The most preferred isomers are those in which the hydroxymethyl group is cis to the purine in compounds of formula (I). It is to be understood that the GA-RTIs of the present invention encompass the individual enantiomers of the compounds of formula (I) as well as wholly or partially racemic mixtures of such enantiomers even though the precise structures as drawn relate to one enantiomer.

In a preferred embodiment, the GA-RTI is selected from the following: (=)-cis4-[2-amino-6-(cyclopropylamino)-9H- purin-9-yl]-2-cyclopentene-1-methanol and racemic or partially resolved mixtures with the (+)-cis enantiomer thereof; and (−)-cis-4-[2-amino-6-(cyclopropylmethylamino)-9H-purin-9-yl]-2-cyclopentene-1-methanol and racemic or partially resolved mixtures with the (+)-cis enantiomer thereof.

These GA-RTIs are particularly preferred because of the high levels which reach the central nervous system where manifestations of HIV infection are particularly debilitating.

The guanosine analog reverse transcriptase inhibitor may be a derivative selected from the group consisting of carboxylic acid esters, sulfonate esters, amino acid esters, and mono-, di-, and triphosphate esters and salts.

In a preferred embodiment, the GA-RTI compound is abacavir (II):

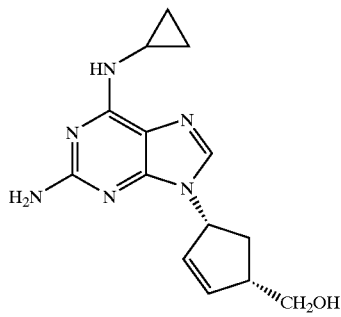
(II)

Abacavir sulfate (tradename "ZIAGEN™"; Glaxo Wellcome, Inc., Research Triangle Park, N.C.) is a synthetic carbocyclic nucleoside analog within the general formula (II) with inhibitory activity against HIV. The chemical name of abacavir sulfate is (1S,cis)-4-[2-amino-6-(cyclopropylamino)-9H-purin-9-yl]-2-cyclopentene-1-methanol sulfate. Abacavir sulfate is the enantiomer with (1S,4R) absolute configuration at the cyclopentene ring. It has a molecular formula of $(C_{14}H_{18}N_6O)_2 \cdot H_2SO_4$ and a molecular weight of 670.76 daltons (see the ZIAGEN™ package insert, the entire disclosure of which is incorporated herein by reference).

Additional related GA-RTI compounds of useful in the synergistic compositions and methods of the present invention are disclosed in U.S. Pat. Nos. 5,631,370, Optically Active Isomers of Dideoxycarbocyclic Nucleosides, issued May 20, 1997; 5,637,574, "Therapeutic Nucleosides," issued Jun. 10, 1997; 5,641,889, same title, issued Jun. 24, 1997; the disclosures of all of which are hereby incorporated herein in their respective entireties.

In other embodiments, the GA-RTI compound is selected from guanosine analogs disclosed in U.S. Pat. Nos. 5,684,010, "Enantiomerically pure beta-D-dioxolane nucleosides with selective anti-hepatitis B virus activity," issued Nov. 4, 1997; 5,834,474, same title, issued Nov. 10, 1998; 5,830,898, same title, issued Nov. 3, 1998; 5,444,063, same title, issued Aug. 22, 1995; 5,179,104, same title, issued Jan. 12, 1993; 5,767,122, "Enantiomerically pure beta-D-dioxolane nucleosides," issued Jun. 16, 1998; and 5,276,151, "Method of synthesis of 1,3-dioxolane nucleosides," issued Jan. 4, 1994.

In a preferred example of an embodiment as described in the preceding paragraph, the GA-RTI compound is DAPD (1-beta-D-2,6-diaminopurine dioxolane, Triangle Pharmaceuticals Inc., Research Triangle Park, N.C.):

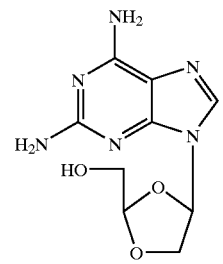
(III)

Inosine Monophosphate Dehydrogenase Inhibitors

Inosine-5'-monophosphate dehydrogenase (IMPDH) is an enzyme in the de novo synthesis pathway of guanosine nucleotides. IMPDH catalyzes the NAD-dependent oxidation of inosine-5'-monophosphate (IMP) to xanthosine-5'-monophosphate (XMP). Two isoforms of human IMPDH have been identified. Type I is constitutive; Type II is inducible and is important in B- and T-lymphocytes. The IMPDH inhibitors useful in the practice of the present invention are potent inhibitors of Type II IMPDH.

The IMPDH inhibitors useful in the practice of the invention preferably have high potency for inhibition of IMPDH enzyme activity. In preferred embodiments, the IMPDH inhibitors have $K_i$ less than about 1 μM, and more preferably have Ki less than about 100 nM. In the most preferred embodiments, the IMPDH inhibitors have $K_i$ less than about 50 nM.

Mycophenolic acid is a potent and lymphocyte-selective inhibitor of de novo purine synthesis. IMPDH inhibitors useful in the practice of the invention may be selected from mycophenolic acid and pharmaceutically acceptable salts, prodrugs, and derivatives, and mycophenolic acid analogs and pharmaceutically acceptable salts, prodrugs, and derivatives. Such compounds, their preparation, and their pharmaceutical compositions and dosage formulations are described in the following United States patents, the disclosures of which are hereby incorporated herein in their respective entireties:

| U.S. Pat. No. | Issued: | Entitled: |
| --- | --- | --- |
| 5,688,529 | Nov. 18, 1997 | Mycophenolate mofetil high dose oral suspensions |
| 5,633,279 | May 27, 1997 | 5-Substituted derivatives of mycophenolic acid |
| 5,554,612 | Sep. 10, 1996 | 4-Amino-6-substituted mycophenolic acid and derivatives |
| 5,554,384 | Sep. 10, 1996 | High dose formulations of mycophenolate mofetil and mycophenolic acid |
| 5,545,637 | Aug. 13, 1996 | Process for preparing pharmaceutical compositions containing crystalline anhydrous mycophenolate mofetil |

-continued

| U.S. Pat. No. | Issued: | Entitled: |
| --- | --- | --- |
| 5,543,408 | Aug. 6, 1996 | Crystalline anhydrous mycophenolate mofetil and intravenous formulation thereof |
| 5,538,969 | July 23, 1996 | 4-Amino derivatives of 5-substituted mycophenolic acid |
| 5,536,747 | July 16, 1996 | 6-Substituted mycophenolic acid and derivatives |
| 5,493,030 | Feb. 20, 1996 | 5-Substituted derivatives of mycophenolic acid |
| 5,455,045 | Oct. 3, 1995 | High dose formulations |
| 5,444,072 | Aug. 22, 1995 | 6-Substituted mycophenolic acid and derivatives |
| 5,441,953 | Aug. 15, 1995 | 4-Amino derivatives of mycophenolic acid |
| 5,380,879 | Jan. 10, 1995 | Derivatives of mycophenolic acid |
| 5,247,083 | Sep. 21, 1993 | Direct esterification of mycophenolic acid |
| 4,861,776 | Aug. 29, 1989 | Heterocyclic aminoalkyl esters of mycophenolic acid and derivatives thereof, compositions and use |
| 4,753,935 | June 28, 1988 | Morpholinoethylesters of mycophenolic acid and pharmaceutical compositions |
| 4,748,173 | May 31, 1988 | Heterocyclic aminoalkyl esters of mycophenolic acid and derivatives thereof and pharmaceutical compositions |
| 4,727,069 | Feb. 23, 1988 | Heterocyclic aminoalkyl esters of mycophenolic acid, derivatives thereof and pharmaceutical compositions |
| 4,725,622 | Feb. 16, 1988 | Mycophenolic acid derivatives in the treatment of rheumatoid arthritis |
| 4,686,234 | Aug. 11, 1987 | Mycophenolic acid derivatives in the treatment of inflammatory diseases, in particular rheumatoid arthritis |

Mycophenolic acid has the formula (IV):

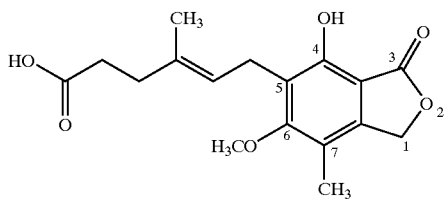

(IV)

Mycophenolic acid is widely commercially available, e.g., from Calbiochem Corporation, Fluke Chemie AG, Indofine Chemical Company, Inc., Sigma Chemical Company, and Roche Labs.

Related compounds include mycophenolic alcohol (V):

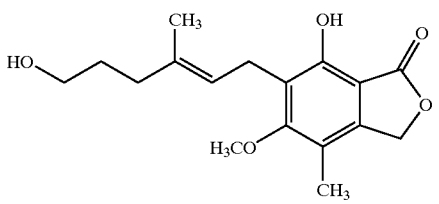

(V)

Analogs of mycophenolic acid that have high IMPDH-inhibiting activity are also useful in the practice of the present invention include compounds with varying substituents in the 4-, 5-, and 6-positions on the mycophenolate core structure, as well as pharmaceutically acceptable salts, derivatives, prodrugs, and metabolites of such mycophenolate analogs. Such compounds are described extensively in the U.S. patents tabulated above and incorporated herein by reference.

The inventors of these above-referenced patents (Nelson, P. H. et al., J Med Chem 1996 October 11;39(21):4181–96) reported the structure-activity relationships in the region of the phthalide ring of mycophenolic acid. Replacement of the lactone ring with other cyclic moieties resulted in loss of potency, especially for larger groups. Replacement of the ring by acyclic substituents also indicated a strong sensitivity to steric bulk. A phenolic hydroxyl group, with an adjacent hydrogen bond acceptor, was found to be essential for high potency. The aromatic methyl group was essential for activity; the methoxyl group could be replaced by ethyl to give a compound with 2–4 times the potency of mycophenolic acid in vitro and in vivo.

The effects of modifying the side chain were also reviewed by the same authors (Nelson, P. H. et al., J Med Chem 1990 February;33(2):833–8). The side-chain appeared more intolerant of variation: twelve side-chain variants of mycophenolic acid were made either from mycophenolic acid itself or from 5-(chloromethyl)-1,3-dihydro4-hydroxy-6-methoxy-7-methyl-3-oxoisobenzofuran. Replacement of the methylated E double bond of the natural product with a triple bond, a Z double bond, a saturated bond, or a sulfur atom, with overall chain lengths equal to or greater than that of mycophenolic acid, produced compounds devoid of significant activity. Replacement of the side-chain double bond with difluoro, dibromo, or unsubstituted cyclopropane rings also removed most activity. Replacement of the double bond with an allenic linkage yielded a compound with about one-fifth of the immunosuppressive activity of mycophenolic acid.

The potential utility of the analogs is evaluated straightforwardly by skilled practitioners using the cell culture assays described herein below and IMPDH-inhibition assay as described, e.g., in U.S. Pat. No. 5,633,279 and others of those listed above.

In an especially preferred embodiment, the mycophenolate IMPDH inhibitor is mycophenolate mofetil (VI), the 2-morpholinoethyl ester of (IV):

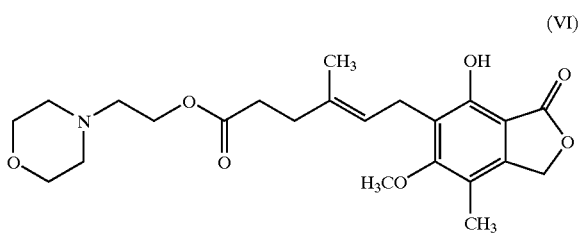

(VI)

Mycophenolate mofetil (Cellcept®), abbreviated "MA" herein, is the 2-morpholinoethylester prodrug of mycophenolic acid. Mycophenolate mofetil is currently approved for use in the prophylaxis of renal allograft rejection, and is in wide clinical use in solid organ transplantation. In such applications, a typical dosage is 2–3 g per day.

Ichimura and Levy (Ichimura H, Levy J. A. Polymerase substrate depletion: a novel strategy for inhibiting the replication of the human immunodeficiency virus. Virology 1995;211(2):554–60) demonstrated that 1–10 µM mycophenolate mofetil, similar to plasma concentrations obtained clinically, inhibit ed the replication of HIV-1 in vitro, probably via depletion of the cellular guanosine nucleotide pools.

The optimal use of mycophenolates in the treatment of HIV infection is not defined. The doses used for immunosuppression can result in clinical toxicity in HIV-positive patients and often blunts the CD4+T cell repletion engendered by effective antiretroviral therapy. Lower doses appear less effective. These drawbacks may limit the widespread and long-term use of mycophenolate. There is therefore a need in the art for compositions and treatment methods which can advantageously reduce the negative effects of mycophenolate without eliminating the positive therapeutic effects.

Mycophenolic acid acts to reversibly inhibit inosine monophosphate dehydrogenase (IMPDH), a critical enzyme in the de novo synthesis of purines limiting the rate of de novo synthesis of guanosine nucleotides (Allison A. et al., 1991; see also Goodman & Gillman's Pharmaceutical Basis of Therapeutics, pp. 1301–1302 (1996) (the entire disclosure of which is incorporated herein by reference). Mycophenolic acid is selective due to the dependence of lymphocyte proliferation on de novo purine synthesis and the presence of the Type II isoform of IMPDH in stimulated lymphocytes that is four times more sensitive to mycophenolic acid than the isoform predominant in other cell lineages (Carr, S. F., Papp, E., Wu, J. C., Natsumeda, Y. Characterization of human type I and type II IMP dehydrogenases. J. Biol. Chem. 268: 27286–90, 1993). $K_i$ values have been reported in the range of 2–10 nM (see for example, Page, J. D. et al., Biochim Biophys Acta 1987 November 6;926(2):186–94; Lesiak, K et al., J Med Chem 1998 February 12;41(4):618–22) and inhibition has been reported to be reversibly uncompetitive or of mixed competitive/uncompetitive character.

In addition to potency of IMPDH inhibition, pharmacologic properties may also be taken into consideration in the selection of the IMPDH inhibitor for incorporation into the synergistic combinations useful in the practice of the invention. Mycophenolic acid and prodrug compounds such as mycophenolate mofetil that are metabolized to mycophenolic acid are converted in vivo to the inactive glucuronide. In an effort to maximize the amount of available drug, use of compounds that are more resistant to metabolic breakdown has been proposed, e.g., glucuronidation-resistant analogs have been synthesized (Lesiak, K., et al. J. Med. Chem. 41: 618–622, 1998), yielding IMPDH inhibitor with a $K_i$ of about 300 nM.

Other IMPDH-inhibiting compounds useful in the practice of the invention are described in U.S. Pat. No. 5,807,876, issued Sep. 15, 1998, "Inhibitors of IMPDH Enzyme," the disclosure of which is hereby incorporated herein in its entirety. The IMPDH inhibitor compounds disclosed therein are reported to be potent inhibitors with good pharmacologic properties. Some of the inhibitors had $K_i$ as low as 15 nM. Included in this class is the potent IMPDH inhibitor VX-497, produced by Vertex Pharmaceuticals, Inc. of Cambridge, Mass.

Nucleoside analogs such as tiazofurin (chemical name), ribavirin (chemical name), and mizoribine also inhibit IMPDH (L. Hedstrom et al. Biochemistry 29: 848–854, 1990). However, these compounds, which are competitive inhibitors of IMPDH, suffer from lack of specificity for this enzyme. Further, for these compounds the $K_i$ for enzyme inhibition is typically in the range of 0.1 to several µM or greater.

Other IMPDH inhibitors useful according to the present invention include the nicotinamide adenine dinucleotide (NAD) analogues of Pankiewicz et al. disclosed in Pharmacol Ther. October–December 1997; 76(1–3):89–100. These analogues contain 5-beta-D-ribofuranosylnicotinamide (C-NAD), 6-beta-D-ribofuranosylpicolinamide (C-PAD), 3-beta-D-ribofuranosylbenzamide (BAD), and 2-beta-D-ribofuranosylthiazole4-carboxamide (TAD) in place of the nicotinamide riboside moiety, and are reported to have potent inhibitory activity against the enzyme in the form of pyrophosphates, as well as metabolically stable methylene-anddifluoromethylenebis(phosphonate)s. Fluorination at the C2' (ribo and arabino configuration) and C3' (ribo) of the adenosine moiety of TAD yields analogues highly potent against IMPDH. Further, NAD analogues containing difluoromethylene linkage are highly effective in inhibition of K562 cell growth, as well as potent inducers of K562 cell differentiation.

Method for Combating a Viral Infection

The present invention provides synergistic compositions and methods of using such compositions for combating viral infections. The viral infections combated using the synergistic compositions and methods of the present invention are preferably retroviral infections and are more preferably HIV infections.

The selection of the GA-RTI and IMPDH inhibitor for incorporation into the synergistic composition will be based on various factors including potency and pharmacologic properties as described above. In the currently most preferred embodiment, the GA-RTI is abacavir and the IMPDH inhibitor is mycophenolate mofetil.

In general, a suitable dose of the GA-RTI for each of the above-mentioned conditions will be in the range of 3.0 to 120 mg per kilogram body weight of the recipient (e.g. a human) per day, preferably in the range of 6 to 90 mg per kilogram body weight per day and most preferably in the range 15 to 60 mg per kilogram body weight per day. Where the GA-RTI is a guanosine analogue of formula (I), the all weight is calculated as the parent compound of formula (I); for salts or esters thereof, the weights would be increased proportionally.) The desired dose is preferably presented as two, three, four, five, six or more sub-doses administered at appropriate intervals throughout the day. These sub-doses may be administered in unit dosage forms, for example, containing 10 to 1000 mg, preferably 20 to 500 mg, and most preferably 100 to 400 mg of GA-RTI per unit dosage form.

Ideally, the GA-RTI should be administered to achieve peak plasma concentrations of the active compound of from about 0.025 to about 100 μm, preferably about 0.1 to 70 μm, most preferably about 0.25 to 50 μm. This may be achieved, for example, by the intravenous injection of a 0.1 to 5% solution of the GA-RTI, optionally in saline, or orally administered as a bolus containing about 0.1 to about 250 mg/kg of the active ingredient. Desirable blood levels may be maintained by a continuous infusion to provide about 0.01 to about 50 mg/kg/hour or by intermittent infusions containing about 0.4 to about 15 mg/kg of the active ingredient.

While it is possible for the synergistic ingredients to be administered individually, either sequentially or simultaneously, it is preferable to present them together as a pharmaceutical formulation. The formulations of the present invention comprise both synergistic ingredients, as defined above, together with one or more acceptable carriers thereof and optionally other therapeutic agents.

Each carrier must be "pharmaceutically acceptable" in the sense of being compatible with the other ingredients of the formulation and not injurious to the subject.

The present invention also provides a synergistic method for the treatment or prophylaxis of a viral infection such as an HIV viral infection or an hepadnaviral infection such as hepatitis B or a herpes viral infection such as CMV, which method comprises administering to the subject with a therapeutically effective amount of the synergistic compunds according to the invention. The methods of the present invention are "synergistic" in that they comprise the administration of the synergistic compounds of the present invention, either individually or together as synergistic compositions.

Examples of retroviral infections which may be treated or prevented in accordance with the invention include human retroviral infections such as human immunodeficiency virus (HIV), HIV-1, HIV-2 and human T-cell lymphotropic virus (HLTV), e.g. HTLV-I or HTLV-II infections. The synergistic compounds, compositions and methods according to the invention are especially useful for the treatment of AIDS and related clinical conditions such as AIDS-related complex (ARC), progressive generalized lymphadenopathy (PGL), AIDS-related neurological conditions, such as multiple sclerosis or tropical paraparesis, anti-HIV antibody-positive and HIV-positive conditions and thrombocytopenic purpura.

The synergistic compounds of the present invention are also useful for the treatment of asymptomatic infections or diseases in humans caused by or associated with human retroviruses.

The therapeutic combinations according to the invention and their pharmaceutically acceptable derivatives may be employed in combination with other therapeutic agents for the treatment of viral infections or conditions. Examples of such further therapeutic agents include agents that are effective for the treatment of viral infections or associated conditions such as acyclic nucleosides (e.g. acyclovir), immunomodulatory agents such as thymosin, ribonucleotide reductase inhibitors such as 2-acetylpyridine 5-[2-chloroanilino) thiocarbonyl) thiocarbonohydrazone, interferons such as alpha-interferon, and phosphonoformic acid. The component compounds of such combination therapy may be administered simultaneously, in either separate or combined formulations, or at different times, e.g. sequentially such that a combined effect is achieved.

In one aspect the compositions and methods of the present invention further comprise a pharmaceutically effective amount of a therapeutic agent selected from the group consisting of didanosine (ddI), zalcitabine (ddC), stavudine (d4T), nevirapine (NVP), delavirdine (DLV), saquinavir, indinavir, ritonavir, and nelfinavir.

In another aspect, the compositions and methods of the present invention exclude the use of zidovodine (AZT) and/or stavudine (D4T).

Abacavir is a novel and potent nucleoside analog reverse transcriptase inhibitor, producing drops in HIV-1 viral RNA similar to those produced by protease inhibitors. We show that low concentrations of MA greatly enhance the effect of abacavir. MA at 0.5 μM resulted in a dramatic decline of HIV production when combined with abacavir in peripheral blood mononuclear cell or macrophage cultures. This effect was seen when laboratory viral strains or primary clinical isolates were tested. Interaction modeling shows a synergy score of 8.2. This synergy is nearly 8 times greater that demonstrated by the combination of abacavir and amprenavir (Drusano G. L., D'Argenio D. Z, Symonds W, Bilello P. A., McDowell, J., Sadler, B., Bye, A., and Bilello, J. A. Nucleoside analog 1592U89 and human immunodeficiency virus protease inhibitor 141W94 are synergistic in vitro. Antimicrob. Agents Chemother 1998; 42:2153–2159), a therapeutic combination that appears potently synergistic in early clinical trials (Schooley R. T. and the 141W94 International Working Group. Preliminary data from a phase I/II study on the safety and antiviral efficacy of the combination of 141W94 and 1592U89 in HIV-infected patients with 150–400 CD4+cells/mm$^3$. In Abstracts of the 4th Conference on Retroviruses and Opportunistic Infections).

The inventive synergistic combinations of abacavir and mycophenolates provide a novel and potent therapeutic combination for use in the treatment of HIV infection. The synergistic combinations are also advantageously characterized in that concentrations of up to 10 μM of MA do not inhibit neutrophil function (Allison A. C., Kowalski W. J., Muller C. D., Eugui E M. Mechanisms of action of mycophenolic acid. Ann NY Acad Sci 1993; 696:63–87); furthermore, high concentrations of MA do not disrupt IL-2 receptor signaling (previous reference; also see Dayton, J. S., Turka, L. A., Thompson, C. B., Mitchell, B. S. Comparison of the effects of mizoribine with those of azathioprine, 6-mercaptopurine, and mycophenolic acid on T-lymphocute proliferation and purine ribonucleotide metabolism. Mol. Pharmacol 1992;41:671–676).

In patients infected with viral strains having more than 2 mutations in the reverse transcriptase gene, a decrease in the response to abacavir may be observed. The use of mycophenolate with abacavir may allow the large patient population with significant antiretroviral experience to benefit from abacavir therapy.

The optimum dose of IMPDH inhibitor used in the treatment of HIV will reflect a balance between the minimal concentration of IMPDH inhibitor needed for synergistic inhibition of reverse transcription, and a concentration of IMPDH inhibitor that induces a beneficial antiproliferative effect without inducing toxicity. Additionally, the use of IMPDH inhibitor with other antiretrovirals must be carefully considered. Clearly, where the IMPDH inhibitor is MA, the concomitant use of thymidine analogs such as AZT or D4T is to be avoided, due to the antagonism of MA and these agents.

Routes of Administration and Dosage Forms

The present invention provides compositions comprising the synergistic compounds, as well as methods of combating viral infection comprising administering said compositions and/or administering the synergistic compounds separately, either simultaneously or consecutively. The synergistic compositions include at least one GA-RTI and at least one IMPDH inhibitor, preferably an MA compound.

The synergistic compounds and compositions according to the invention may be administered for therapy by any suitable route including oral, rectal, nasal, topical (including transdermal, buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

Pharmaceutical formulations of the present invention include those suitable for oral, rectal, nasal, topical (including transdermal buccal and sublingual), vaginal or parenteral (including subcutaneous, intramuscular, intravenous and intradermal) administration.

The formulations may conveniently be presented in unit dosage form and may be prepared by methods known in the art of pharmacy. Such methods include the step of bringing into association the synergistic ingredients with the carrier. The carrier optionally comprises which constitutes one or more accessory ingredients. In general, the formulations are prepared by uniformly and intimately bringing into association the synergistic ingredients with liquid carriers or finely divided solid carriers or both, and then if necessary shaping the product.

Compositions suitable for transdermal administration may be presented as discrete patches adapted to remain in intimate contact with the epidermis of the recipient for a prolonged period of time. Such patches suitably contain the synergistic ingredients compound 1) in an optionally buffered, aqueous solution, 2) dissolved and/or dispersed in an adhesive or 3) dispersed in a polymer. A suitable concentration of each synergistic ingredient is about 1% to 25%, preferably about 5 to 15%. The active compound may also be delivered from the patch by electrotransport or iontophoresis as generally described in Pharmaceutical Research, 3 (6), 318 (1986) (the entire disclosure of which is incorporated herein by reference).

Formulations of the present invention suitable for oral administration may be presented as discrete units such as capsules, caches or tablets, each containing a predetermined amount of the synergistic ingredients; as a powder or granules; as a solution or a suspension in an aqueous or non-aqueous liquid; or as an oil-in-water liquid emulsion or a water-in-oil liquid emulsion. The synergistic ingredients may also be presented as a bolus, electuary or paste.

A tablet may be made by compression or molding, optionally with one or more accessory ingredients. Compressed tablets may be prepared by compressing in a suitable machine the synergistic ingredients in a free-flowing form such as a powder or granules, optionally mixed with a binder (e.g. povidone, gelatin, hydroxypropylmethyl cellulose), lubricant, inert diluent, preservatives, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of one or more of the synergistic ingredients therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising one or more of the synergistic ingredients in a flavored basis, usually sucrose and acacia or tragacanth; pastilles comprising one or more of the synergistic ingredients in an inert basis such as gelatin and glycerin, or sucrose and acacia; and mouthwashes comprising the one or more of the synergistic ingredients in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the one or more of the synergistic ingredients such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as described herein, or an appropriate fraction thereof, of one or more of the synergistic ingredients.

It should be understood that, in addition to the ingredients particularly mentioned above, the formulations of this invention may include other agents conventional in the art having regard to the type of formulation in question; for example, those suitable for oral administration may include such further agents as sweeteners, thickeners and flavoring agents.

Experimental Assays

Drugs and Viral Isolates

Mycophenolic acid (MA), 2',3'-dideoxycytidine (ddC), didanosine (DDI), and zidovudine (AZT) were obtained from Sigma (St. Louis, Mo.). Stavudine (D4T) was a gift of Bristol-Meyers Squibb (Princeton, N.J.). Abacavir was provided by Glaxo Wellcome, Inc. (Research Triangle Park, N.C.). The HIV-1 T-cell line adapted isolate IIIb (Popovic M, Sarngadharan M G, Read E, Gallo R C. Detection, isolation, and continuous production of cytopathic retroviruses (HTLV-III) from patients with AIDS and pre-AIDS. Science 1984;224:497), the macrophage-tropic isolate SF162 (Chenge-Mayer C, Levy J. A. Distinct biological and serological properties of human immunodefiency viruses from the brain. Ann Neuro 1988;23:S58), and the $LAI_{184V}$ isolate (a resistant clone containing the M184V mutation: Schinazy R. F., Lloyd R. M. Jr., Nguyen M. H., Cannon D. L., Iiksoy N, Chu C. K., Liotta D. C., Bazmi H. Z., Mellors J. W. Characterization of human immunodeficiency viruses resistant to oxathiolance-cytosine nucleosides. Antimicrob Agents Chemother 1993;37:875) were obtained from the National Institutes of Health AIDS Research and Reference Reagent Program (Rockville, Md.). Syncytia-inducing (SI) isolates EJC-X1 and EJC-X2, and the non-syncytia-inducing (NSI) isolate EJC-R1 were obtained under an approved human studies protocol from infected individuals followed at the University of Maryland Medical Center. Stocks from these viruses were prepared using primary peripheral blood mononuclear cells (PBMCs) from normal donors. The $TCID_{50}$ of these stocks was determined in primary PBMCs as described (ACTG Virology Manual, NIH Pub No. 94 3828, 1994). The SI phenotype was determined by assessing viral growth and syncytia formation in the MT-2 cell line (Harada S., Koyanagi Y., Yamamoto N. Infection of HTLV-III/LAV in HTLV-I-carrying cells MT-2 and MT-4 and application in plaque assay. Science 1985; 229:563).

Cell Culture and Viral Infection

Primary PBMCs were separated from whole blood of HIV seronegative donors by density centrifugation over Ficoll-Hypaque (Sigma). The culture medium consisted of RPMI supplemented with 10% fetal bovine serum (FBS), 2 mM glutamine and penicillin/streptomycin (Gibco, Grand Island, N.Y.). For infection studies involving PBMCs, cells were stimulated with 10 µg/mL phytohemagglutinin (PHA; Boehringer Mannheim, Indianapolis, Ind.) and cultured for 3 days. Stimulated PBMCs were infected by incubation with virus at a multiplicity of infection of 1000 $TCID_{50}/d10^6$ PBMC for 2 hours. PBMC were then washed three times with PBS and cultured in 5% $CO_2$ at 37° C, in RPMI/10% FBS supplemented with 10 units/mL IL-2 (Boehringer Mannheim) and drugs as appropriate. PBMC were seeded in 96-well flat-bottom plates at a density of $2\times10^5$ PBMC/200 µL. Following three days of culture, half of the medium was replaced with fresh medium containing IL-2 and drugs. After 7 days of culture HIV-1 p24 production in the culture supernatant was assayed by ELISA (Coulter, Hialeah, Fla.).

The HIV-1 strain SF162 was used for infection of macrophages derived from primary blood monocytes as described by Perno and Yarchoan (Perno C.-F, Yarchoan R. Culture of HIV in monocytes and macrophages in Current Protocols in Immunology 1993 Suppl.5, 12.4.4–12.4.5). Briefly, $25\times10^6$ PBMCs were cultured for 5 days in T-25 flasks (Corning Costar, Cambridge, Mass.) containing culture medium supplemented with 20% FBS and 10% AB human serum (Gemini Bioproducts, Inc., Calabasas, Calif.). On day 5 non-adherent cells were removed by washing five times with warm medium. Adherent cells were counted by trypan blue exclusion. HIV infection was carried out by adding virus to the flasks at a multiplicity of infection of 2000 $TCID_{50}/10^6$ adherent cells and incubating for 3 hours. Flasks were then washed 3 times with warm medium and cultured in RPMI containing 20% FBS. Medium was replaced every 3 days. HIV-1 p24 production in the culture supernatant was assayed after 10 days.

Cellular proliferation in culture in the presence or absence of MA and abacavir was measured using a commercial MMT cell proliferation assay, as per the manufacturer's instructions (Boehringer Mannheim).

Drug Interaction Analysis

Additive antiviral effect was analyzed according to the definition of Loewe, using the interaction model of Greco et al. as was described above. This model is fully parametric, and point estimates of the model parameters are obtained in a traditional weighted, nonlinear least-squares approach. The model follows the equation below:

$$1 = \frac{D_1}{IC_{50.1} \cdot [E/(E_{con} - E)]^{1/m1}} + \frac{D_2}{IC_{50.2} \cdot [E/(E_{con} - E)]^{1/m2}} + \frac{\alpha \cdot D_1 \cdot D_2}{IC_{50.1} \cdot IC_{50.2} \cdot [E/(E_{con} - E)]^{(1/2m1+1/2m2)}}$$

where α (alpha) is the synergism-antagonism interaction parameter, $IC_{50.1}$ and $IC_{50.2}$ are the drug concentrations resulting in 50% inhibition for drug 1 and drug 2, respectively; D1 and D2 are the concentration of drugs tested; Econ is the control effect in the absence of either drug, E is the observed effect, and m 1 and m 2 are the slope parameters for each drug. If the estimate of α is zero, the drug combination is additive; if α is positive, the interaction is synergistic; if α is negative, the interaction is antagonistic. When the 95% confidence interval for α does not overlap zero, this demonstrates statistical significance of the interaction. That is, if the 95% confidence interval encompasses zero, the interaction is additive. If it does not and α is positive, the interaction is significantly synergistic. If it does not and ax is negative, the interaction is significantly antagonistic. This model was implemented using the ADAPT II programs (D'Argenio D. Z, Schumitzky A. ADAPT II: a program package for simulation identification and optimal experimental design. 1990. Biomedical Simulations Resource, Univ. Of Southern California, Los Angeles). Each drug combination was tested in triplicate so as to obtain an estimate of the variance of the effect at different drug concentration combinations.

EXAMPLE 1

Abacavir and MA Synergistically Inhibit HIV-1 in Peripheral Blood Mononuclear Cells (PBMCS)

The combined effect of abacavir and MA was examined in PBMC culture systems. PBMCs from a seronegative donor were stimulated with PHA and infected with the T-cell tropic isolate HIV-1 IIIb. At the clinically utilized dose (600 mg/day) of abacavir steady state peak serum levels are 3 µg/mL (4.47 µM; e.g.,see Ziagen package insert. Glaxo Wellcome, Inc., Research Triangle Park, N.C.). After a single 1000 mg dose of MA in a healthy individual, the mean peak serum level is 56.5 µM. Therefore, infected cells were cultured in the presence of abacavir from 0 to 4 µM, and in the presence of 0 to 1 µM of MA. On day 7 after infection the number of viable cells was determined by MTT assay (Boehringer Mannheim), and p24 antigen in the culture supernatant was measured.

Figure 1B:
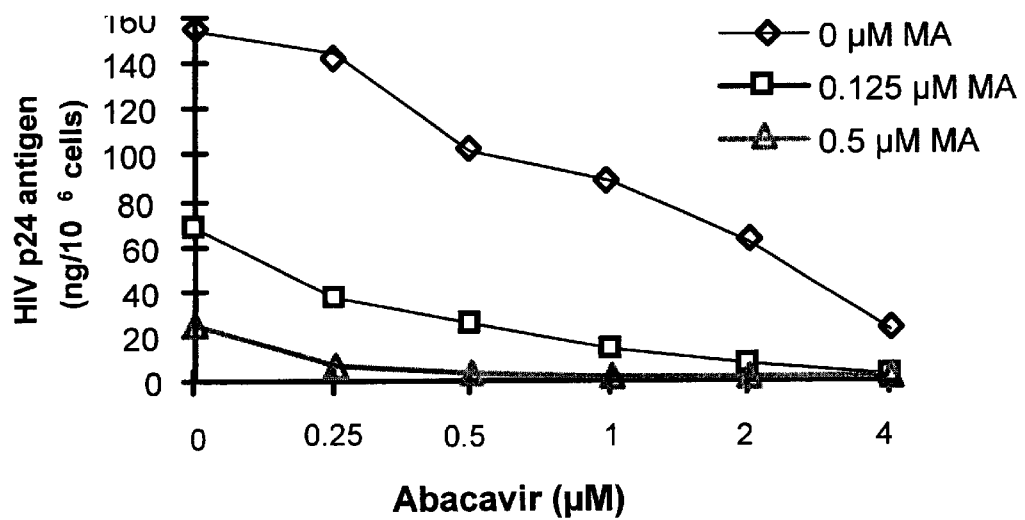

FIGS. 1A and 1B are plots of p24 production in the HIV IIIb infected peripheral blood mononuclear cells versus abacavir concentration (EM) at 0, 0.06, 0.125, 0.25, 0.5, and 1 µM MA (FIG. 1A) and at 0, 0.125 and 0.500 µM MA (FIG. 1B). To account for the possibility that the inhibition of HIV production was due primarily to an antiproliferative effect of MA, the data in FIG. 1B is displayed as p24 antigen per $10^6$ cells. The synergism of MA and abacavir is readily apparent. For example, in the presence of 0.125 µM of MA, 16-fold less abacavir was required for profound inhibition of HIV IIIb. The effect of 0.5 µM of MA was even more striking.

The interaction of abacavir and MA in the suppression of HIV IIIb replication in PBMCs was analyzed using the Greco model as described above. Each data point was determined in triplicate. Each observation was weighted by the inverse of the observation variance. These parameters and their 95% confidence bounds are shown below:

| Value | $E_{con}$ (%) | $IC_{50}$ MA (µM) | m MA | $IC_{50}$ abacavir (µM) | m abacavir | Alpha value |
|---|---|---|---|---|---|---|
| Estimate | 165.7 | 0.11 | 1.90 | 0.63 | 0.70 | 8.21 |
| 95% C.I. | 141.2–190.3 | 0.09–0.13 | 1.62–2.19 | 0.26–0.99 | 0.58–0.81 | 3.07–13.34 |

Figure 2:
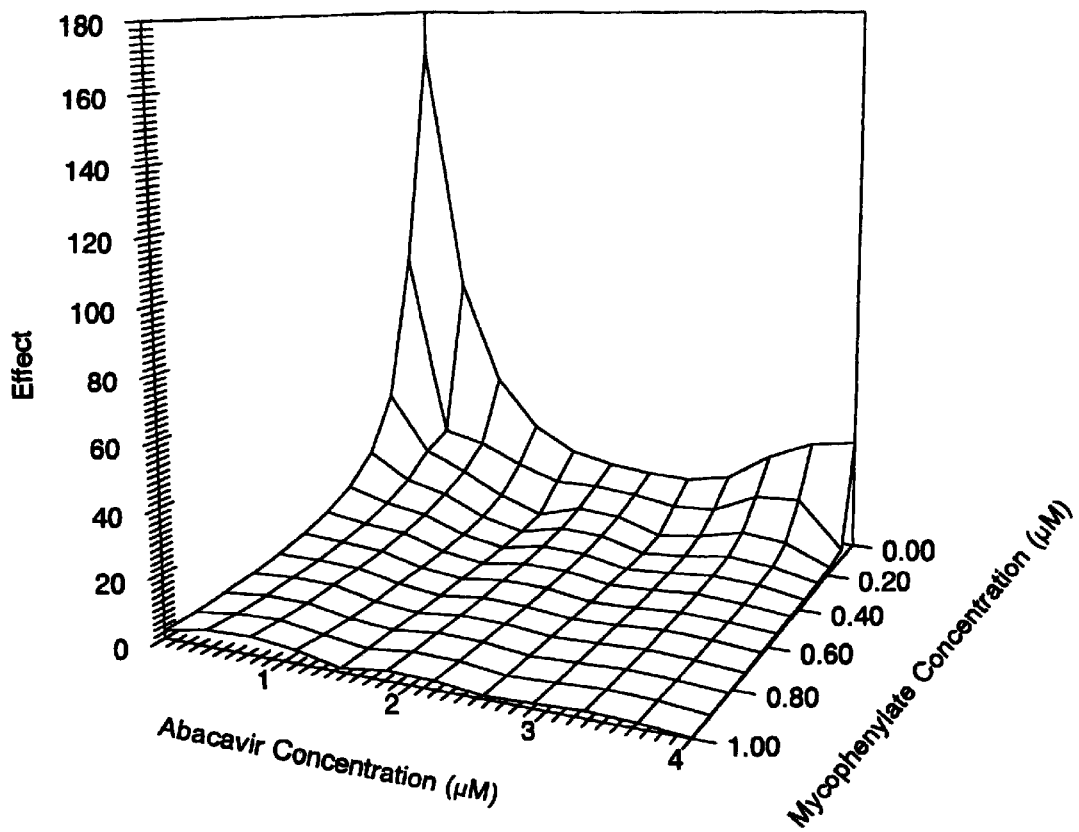
FIG. 2 is a three-dimensional response surface of the mycophenolate mofetil and abacavir combination matrix, displaying data from FIG. 1.

The $IC_{50}$ of abacavir was found to be 0.626 µM, while that of MA was 0.1 µM. The value obtained for the interaction parameter alpha was 8.205, with a 95% confidence bound of 3.06 to 13.34. These boundaries do not overlap zero, and indicate a degree of synergy nearly 8-fold greater than that estimated for abacavir and the protease inhibitor amprenavir (Drusano G. L., D'Argenio D. Z., Symonds W., Bilello P. A., McDowell, J., Sadler, B., Bye, A., and Bilello, J. A. Nucleoside analog 1592U89 and human immunodeficiency virus protease inhibitor 141W94 are synergistic in vitro. Antimicrob. Agents Chemother 1998;42:2153–2159). The full effect surface of this interaction is displayed in FIG. 2. The weighted difference of the model prediction from the observed data was plotted, and residuals found to scatter about the zero line, indicating an unbiased representation by the parametric model.

EXAMPLE 2

Abacavir and MA Inhibit HIV-1 in Monocyte-derived Macrophages (MOM)

To examine the effect of MA on HIV replication in macrophages, a similar experiment was performed using MDM and the macrophage-tropic strain HIV-1 SF162. Given the variability often observed among seronegative donors in susceptibility to HIV-1 infection of macrophages, MDMs from two different donors were used. Cells were infected with SF162 and cultured in the presence of 0.5 µM of abacavir, with and without 0.5 µM MA. On day 10 after infection virus production was evaluated by p24 antigen assay. Similar results were obtained with the MDM from both donors.

Figure 3:
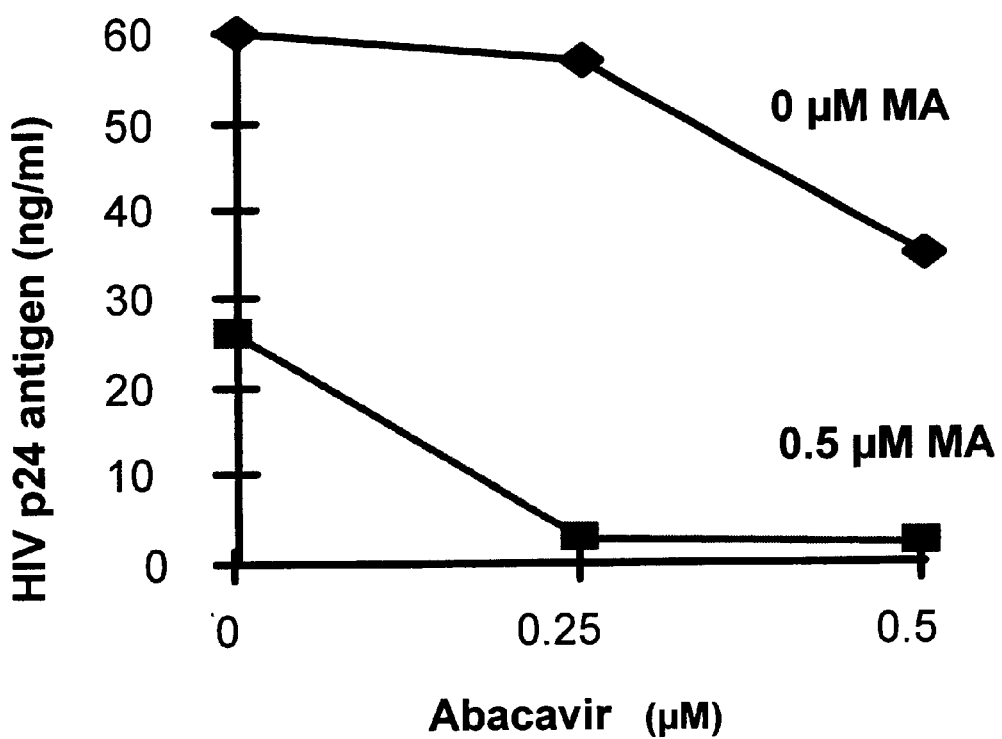
FIG. 3 is a plot of p24 production by HIV SF162 infected macrophages versus abacavir concentration ($\mu$M) at 0 and 0.500 $\mu$M MA.

FIG. 3 is a plot of p24 production by HIV SF162 infected macrophages versus abacavir concentration (µM) at 0 and 0.500 µM MA. A 96% inhibition of viral replication was found when 0.25 µM abacavir was combined with 0.5 µM MA.

In a separate experiment, no effect on viability as determined by trypan blue exclusion was noted in macrophages cultured in the presence of 1 µM MA and 0.5 µM abacavir for 3 weeks (not shown).

EXAMPLE 3

Figure 4:
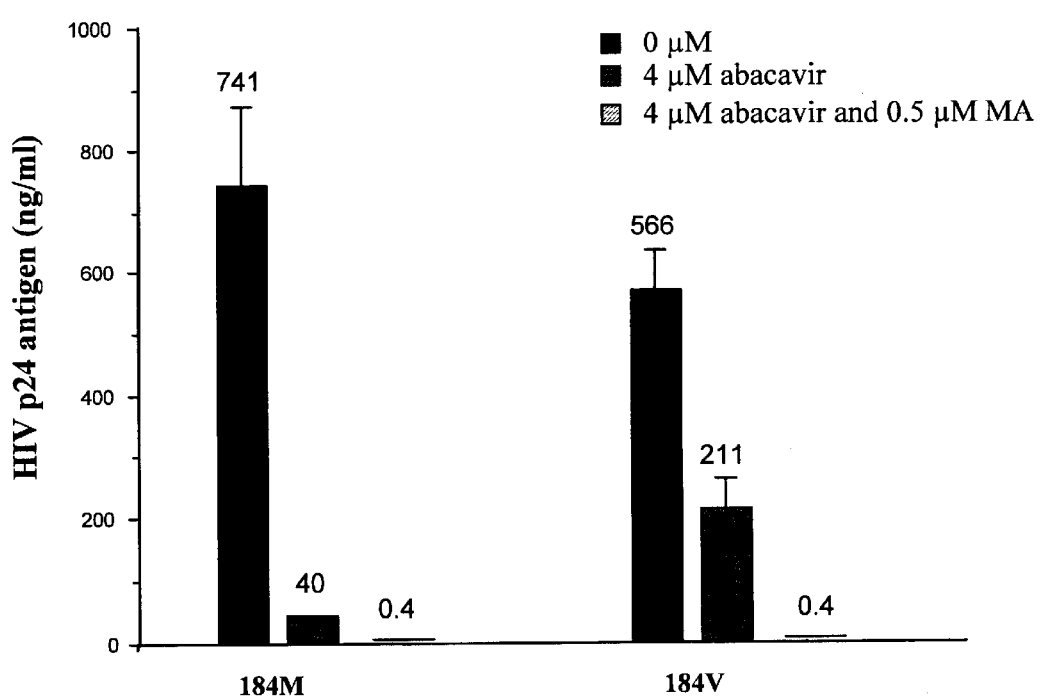
FIG. 4 is a plot of day 7 HIV p24 antigen/mL, showing inhibition of replication of wild-type and M184V mutant HIV-1 by mycophenolate mofetil and abacavir in PBMCs from a seronegative donor which were infected and then cultured in the presence or absence of MA and/or abacavir.

Abacavir and MA Inhibit both HIV Expressing a Reverse Transcriptase that Contains the M184V Mutation and Clinical Isolates A methionine-to-valine change at position 184 of the HIV reverse transcriptase confers high level resistance to 3TC (lamivudine) and 2- to 5-fold resistance to abacavir (Tisdale M., Alnadaf T., Cousens D. Combination of mutations in human immunodeficiency virus type 1 reverse transcriptase required for resistance to the carbocyclic nucleoside 1592U89. Antimicrob. Agents Chemother 1997;41:1094–1098). Depletion of dGTP via inhibition of IMPDH might be predicted to augment the ability of abacavir to inhibit virus encoding the M 184V mutation. Wild-type HIV was inhibited 98% by 4 µM abacavir, and 99.9% following the addition of 0.5 µM of MA. However, resistant HIV encoding M184V was inhibited only 53% by 4 µM abacavir, but 99.7% following the addition of 0.5 µM MA. FIG. 4 is a plot of day 7 HIV p24 antigen/mL, showing inhibition of replication of wild-type and M184V mutant HIV-1 by MA and abacavir in PBMCs from a seronegative donor which were infected and then cultured in the presence or absence of MA and/or abacavir.

The ability of MA to augment the antiviral activity of abacavir was studied in three clinical isolates. Donor PBMCs were infected with 3 different isolates and cultured in presence of abacavir with or without MA. Modest inhibition was seen in the presence of 0.25 µM of abacavir, consistent with the IC50 reported for a panel of clinical isolates (Ziagen™ package insert. Glaxo Wellcome Inc., Research Triangle Park, Inc., N.C.). In all cases profound viral inhibition was observed when 0.25 µM abacavir was combined with 0.25 µM MA; results are tabulated below:

| | | Amount of p24 (ng/mL) measured on day 7 after infection (% inhibition of HIV-1) | | |
|---|---|---|---|---|
| Isolate | MT-2 Phenotype | No drug | Abacavir (0.25 µM) | Abacavir (0.25 µM) + MA (0.25 µM) |
| KAB | SI | 739 | 465 (37) | 41 (94) |
| SBH | SI | 272 | 260 (4) | 32 (88) |
| MSO | NSI | 114 | 46 (59) | 1.4 (98) |

EXAMPLE 4

Effective Antiviral Concentrations of Abacavir and Mycophenolate have Little Effect on Proliferation MA may synergize with abacavir via depletion of cellular guanosine pools, effectively increasing the intracellular concentration of abacavir. However, MA may also act via a general inhibitory effect on T lymphocyte proliferation, as has been hypothesized in the case of hydroxyurea (Lori F., Malykh A. G., Foli A., Maserati R., De Antoni A., Minoli L., Padrini D., Degli Antoni A., Barchi E., Jessen H., Wainberg M. A., Gallo R. C., Lisziewicz J. Combination of a drug targeting the cell with a drug targeting the virus controls human immunodeficiency virus type 1 resistance. AIDS Res Hum Retroviruses 1997; 13(16): 1403–9; De Boer R. J., Boucher C. A., Perelson A. S. Target cell availability and the successful suppression of HIV by hydroxyurea and didanosine. AIDS 1998; 12(13): 1567–70). The addition of deoxyguanosine to the culture media ablated the inhibitory effect of MA, whereas the addition of deoxyadenosine had no effect (not shown).

MTT assays performed at day 2 and day 5 of PBMC cultures showed little inhibition of cellular proliferation in the presence of 0.25 µM MA, an effective antiviral concentration. The left portion of FIG. 5 displays the results of MTT assays performed at day 5 of PBMC cultures, showing the antiproliferative effect of MA at 0.125, 0.25, 0.5 and 1 µM concentrations in the culture media. Similar results were also obtained on day 2 after the addition of MA.

Figure 5:
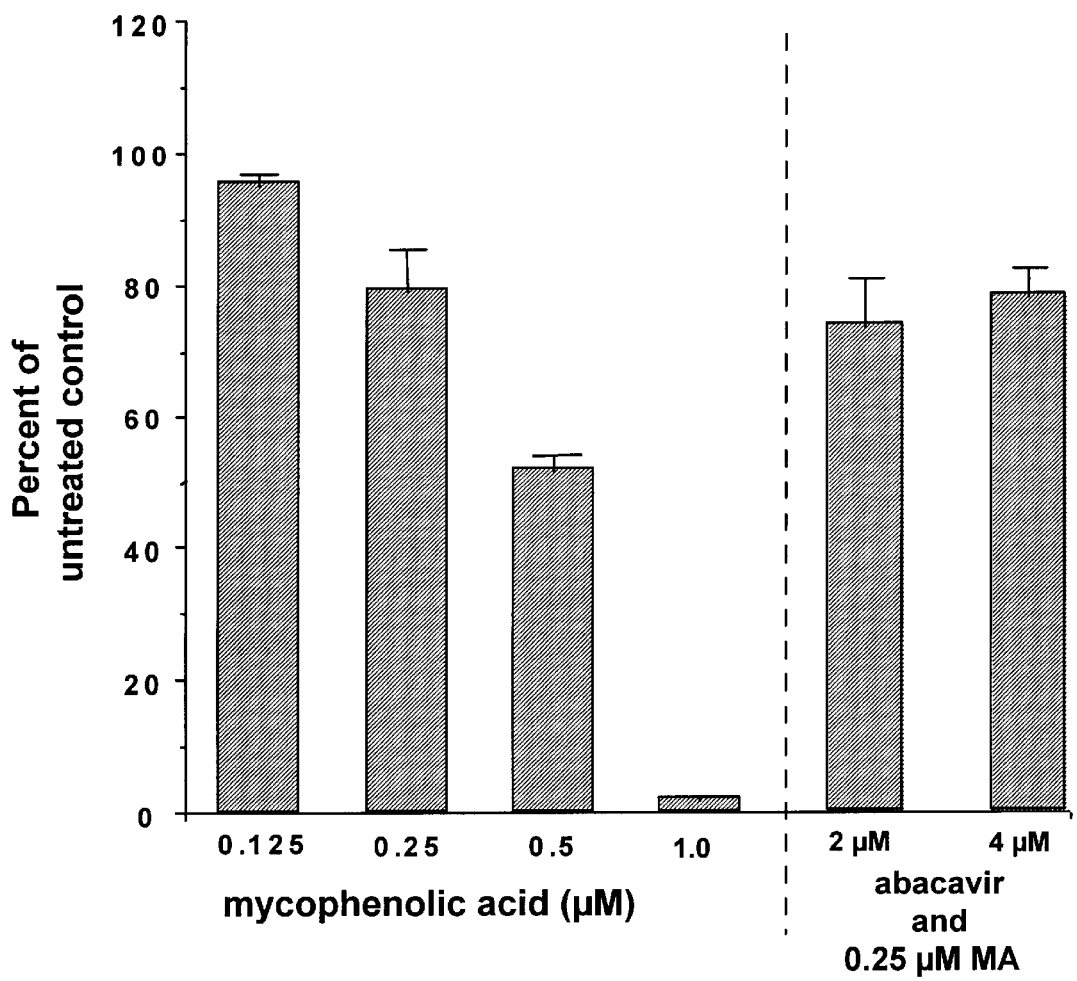
FIG. 5 is a plot of MTT assays performed at day 2 and day 5 of PBMC cultures, showing the antiproliferative effect of MA at 0.125, 0.25, 0.5 and 1 $\mu$M concentrations in the culture media, and also shows the results of MTT assays performed at day 2 and day 5 of PBMC cultures, showing the antiproliferative effect of MA (0.5 $\mu$M) plus abacavir (2 $\mu$M, 5 $\mu$M).

While 0.5 µM MA exerted modest antiproliferative effect, concentrations of abacavir comparable to the peak clinical serum level (2 µM, 4 µM) did not enhance this effect. The right portion of FIG. 5 shows the results of MTT assays performed at day 5 of PBMC cultures, showing the antiproliferative effect of MA (0.5 µM) plus abacavir (2 µM, 5 µM). Similar results were also obtained on day 2 after the addition of MA. These findings suggest that the majority of the antiviral effect mediated by MA is due to inhibition of HIV reverse transcription, and that the clinical combination of these agents might be feasible.

EXAMPLE 5

MA is not Synergistic with all HIV-1 Reverse Transcriptase Inhibitors

Although MA directly depletes cellular guanosine pools through inhibition of IMPDH, this may result secondarily in perturbations of other cellular enzyme activities. Such perturbations could result in beneficial or detrimental therapeutic effects. The combined effects of MA and available nucleoside analogs are described in Table 2:

| | | | |
|---|---|---|---|
| 0.5 μM MA | 2 μM abacavir | combined (predicted) | Combined (observed) |
| 9.3 | 2.7 | 25 | 160 (synergy) |
| 0.5 μM MA | 2 μM stavudine | combined (predicted) | Combined (observed) |
| 9.3 | 115 | 1070 | 63 (antagonism) |
| 0.125 μM MA | xx zidovudine | combined (predicted) | Combined (observed) |
| 1.3 | 84 | 109 | 43 (antagonism) |
| 0.125 μM MA | xx didanosine | combined (predicted) | combined (observed) |
| 1.3 | 11 | 14 | 30 (synergy) |
| 0.5 μM MA | xx zalcitibine | combined (predicted) | combined (observed) |
| 9.3 | 3.9 | 36 | 35 (additive) |

MA was found to exert an additive, but not synergistic, antiviral effect in combination with the cytosine analog zalcitibine. However, MA was significantly antagonistic when combined with the thymidine analogs zidovudine and stavudine. This result may be due to decreased activity of thymidine kinase, and therefore decreased activation of thymidine analogs, induced by IMPDH inhibition as reported for the IMPDH inhibitor ribavirin (Vogt, M. W., K. L. Hartshorrn, P. A. Furman, T.-C. Chou, J. A. Fyfe, L. A. Coleman, C., Crumpacker, R. T. Schooley, and M. S. Hirsch. Ribavirin antagonizes the effect of azidothynidine on HIV replication. Science 1987; 235:1376–1379. Baba M., Pauwels R., Balzarini J., Herdewijn P., DeClercq E., and Desmyter J. Ribavirin antagonizes inhibitory effects of purine 2',3'dideoxynucleosides on replication of human immunodeficiency virus in vitro. Antimicrob. Agents Chemother 1987; 31:1613–1617. Hartman N. R., Ahluwalia G. S., Cooney D. A., Mitsuya H., Kaeyama S., Fridland A., Broder S., and Johns D. G. Inhibitors of IMP Dehydrogenase stimulate the phosphorylation of the anti-human immunodeficiiency virus nucleosides 2',3'-dideoxyadenosine and 2',3'-dideoxyinosine. Molecular Pharmacology 1991; 40:118–124). However the antiviral effect of MA was more than additive in combination with the adenosine analog didanosine (ddI). This may be the result of increased conversion of ddI to ddATP, due to the accumulation of IMP—the major phosphate donor for the initial phosphorylation step in the ddIno to ddATP pathway.

While the invention has been described herein with reference to various illustrative features, aspects and embodiments, it will be appreciated that the invention is susceptible of variations, modifications and other embodiments, other than those specifically shown and described. The invention is therefore to be broadly interpreted and construed as including all such alternative variations, modifications and other embodiments within its spirit and scope as hereinafter claimed.

What is claimed is:

1. A pharmaceutical composition comprising:
   a) at least one guanosine analog reverse transcriptase inhibitor selected from the group consisting of: (−)-cis-4-[2-amino-6-(cyclopropylamino)-9H-purin-9-yl]-2-cyclopentene-1-methanol, a racemic of (−)-cis-4-[2-amino-6-(cyclopropylamino)-9H-purin-9-yl]-2-cyclopentene-1-methanol with the (+)-cis enantiomer thereof, (−)-cis-4-[2-amino-6-(cyclopropylmethylamino)-9H-purin-9-yl]-2-cyclopentene-1-methanol, and a racemic mixture of (−)-cis-4-[2-amino-6-(cyclopropylmethylamino)-9H-purin-9-yl]-2-cyclopentene-1-methanol with the (+)-cis enantiomer thereof; and
   b) at least one inosine monophosphate dehydrogenase inhibitor, wherein the inosine monophosphate dehydrogenase inhibitor is a mycophenolate, and wherein the amount of the inosine monophosphate dehydrogenase inhibitor is less than the amount of the guanosine analog reverse transcriptase inhibitor and the combination provides a synergistic effect in the treatment of viral infections.

2. A pharmaceutical composition comprising
   a) at least one guanosine analog reverse transcriptase inhibitor having the formula:

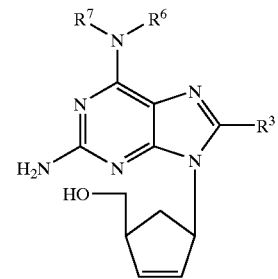

where
   $R^3$ represents hydrogen or $C_1$–$C_6$ alkyl;
   $R^6$ represents $C_{3-8}$ cycloalkyl;
   $R^7$ represents hydrogen or branched or straight chain $C_{1-6}$ alkyl; and
   b) at least one inosine monophosphate dehydrogenase inhibitor, wherein the inosine monophosphate is a mycophenolate, and wherein the inosine monophosphate dehydrogenase inhibitor is in an amount less than the amount of the guanosine analog reverse transcriptase inhibitor thereby providing a synergistic effect in the treatment of viral infections.

3. A pharmaceutical composition according to claim 2 wherein the inosine monophosphate dehydrogenase inhibitor is selected from mycophenolic acid and mycophenolic acid esters.

4. A pharmaceutical composition according to claim 3 wherein the inosine monophosphate dehydrogenase inhibitor is selected from mycophenolic acid and mycophenolate mofetil.

5. A pharmaceutical composition comprising a synergistically effective amounts of:
   a) at least one guanosine analog reverse transcriptase inhibitor, or a pharmaceutically acceptable salt, derivative, or prodrug thereof,
   b) at least one inosine monophosphate dehydrogenase inhibitor, or a pharmaceutically acceptable salt, derivative, or prodrug thereof, and
   c) a pharmaceutically acceptable carrier therefor, wherein the guanosine analog reverse transcriptase inhibitor is selected from the group consisting of: (−)-cis-4-[2-amino-6-(cyclopropylamino)-9H-purin-9-yl]-2- cyclopentene-1-methanol, a racemic of (−)cis-4-[2-amino-6-(cyclopropylamino)-9H-purin-9-yl]-2-cyclopentene-1-methanol with the (+)-cis enantiomer thereof, (−)-cis-4[2-amino-6-(cyclopropylmethylamino)-9H-purin-9-yl]-2-cyclopentene-1-methanol, and a racemic mixture of (−)-cis-4[2-amino-6-(cyclopropylmethylamino)-9H-purin-9-yl]-2-cyclopentene-1-methanol with the (+)-cis enantiomer thereof; wherein the inosine monophosphate dehydrogenase inhibitor is a mycophenolate, and wherein the combination of the inosine monophosphate dehydrogenase inhibitor and guanosine analog reverse transcriptase inhibitor provides a synergistic effect in the treatment of viral infections.

6. A method of treating a viral infection comprising: administering to infected cells a pharmaceutical composition comprising:

a) at least one guanosine analog reverse transcriptase inhibitor having formula:

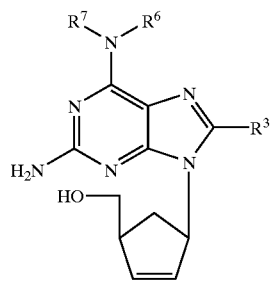

where
$R^3$ represents hydrogen or $C_1$–$C_6$ alkyl;
$R^6$ represents $C_{3-8}$ cycloalkyl;
$R^7$ represents hydrogen or branched or straight chain $C_{1-6}$ alkyl; and b) at least one inosine monophosphate dehydrogenase inhibitor, wherein the inosine monophosphate is a mycophenolate, and wherein the inosine monophosphate dehydrogenase inhibitor is in an amount less than the amount of the guanosine analog reverse transcriptase inhibitor thereby providing a synergistic effect in the treatment of viral infections.

7. A method of manufacturing a pharmaceutical composition comprising bringing into association with a pharmaceutical carrier:

a) at least one guanosine analog reverse transcriptase inhibitor having the formula:

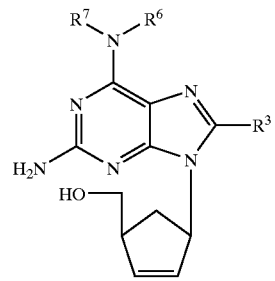

where
$R^3$ represents hydrogen or $C_1$–$C_6$ alkyl;
$R^6$ represents $C_{3-8}$ cycloalkyl;
$R^7$ represents hydrogen or branched or straight chain $C_{1-6}$ alkyl; and b) at least one inosine monophosphate dehydrogenase inhibitor, wherein the inosine monophosphate is a mycophenolate, and wherein the inosine monophosphate dehydrogenase inhibitor is in an amount less than the amount of the guanosine analog reverse transcriptase inhibitor thereby providing a synergistic effect in the treatment of viral infections.

8. A pharmaceutical composition comprising:

a) abacavir; and b) mycophenolic acid and/or ester(s) thereof, and wherein the amount of the mycophenolic acid and/or ester(s) thereof is in an amount less than the amount of the abacavir and the combination provides a synergistic effect in the treatment of viral infections.

9. A method of treating a viral infection comprising: administering to infected cells a pharmaceutical composition according to claim 8.

10. A method of manufacturing a pharmaceutical composition comprising bringing into association with a pharmaceutical carrier the composition according to claim 8.

* * * * *

UNITED STATES PATENT AND TRADEMARK OFFICE
CERTIFICATE OF CORRECTION

PATENT NO. : 6,514,979 B1
DATED : February 4, 2003
INVENTOR(S) : David Margolis, Alonso Heredia, David Oldach and Robert Redfield It is certified that error appears in the above-identified patent and that said Letters Patent is hereby corrected as shown below:

Column 1,
Line 58, "4" should be -- -4 --.

Column 2,
Line 10, "4" should be -- -4 --.

Column 6,
Line 67, "(=)" should be -- (-) --.

Column 8,
Line 39, "Ki" should be -- $K_j$ --.

Column 10,
Line 45, "dihydro4-" should be -- dihydro-4- --.

Column 11,
Line 23, "inhibit" should be -- inhibited --.
Line 50, "$K_i$" should be -- $K_1$ --.

Column 13,
Line 58, "[2-" should be -- [(2- --.

Column 16,
Line 47, "$LAI_{184V}$" should be -- $LAI_{M184V}$ --.
Line 50, "liksoy" should be -- llksoy --.

Column 18,
Line 12, "ax" should be -- a --.
Line 44, "(EM)" should be -- ($\mu M$) --.

UNITED STATES PATENT AND TRADEMARK OFFICE
CERTIFICATE OF CORRECTION

PATENT NO.    : 6,514,979 B1
DATED         : February 4, 2003
INVENTOR(S)   : David Margolis, Alonso Heredia, David Oldach and Robert Redfield It is certified that error appears in the above-identified patent and that said Letters Patent is hereby corrected as shown below:

Column 23,
Line 1, ")cis-4" should be -- )-cis-4 --.

Signed and Sealed this

Eighth Day of April, 2003

JAMES E. ROGAN
*Director of the United States Patent and Trademark Office*